United States Patent [19]

Kobayashi et al.

[11] Patent Number: 5,152,295
[45] Date of Patent: Oct. 6, 1992

[54] FUNDUS EXAMINATION DEVICE

[75] Inventors: Kouji Kobayashi; Itaru Yoshizawa, both of Hino, Japan

[73] Assignee: Kowa Company Ltd., Japan

[21] Appl. No.: 552,785

[22] Filed: Jul. 11, 1990

[30] Foreign Application Priority Data

Jul. 26, 1989 [JP] Japan .................. 1-191313

[51] Int. Cl.$^5$ .............................................. A61B 6/00
[52] U.S. Cl. ................................ 128/665; 351/206; 351/221
[58] Field of Search ............... 128/665, 633; 351/205, 351/206, 207, 208, 221; 354/64; 356/376

[56] References Cited

U.S. PATENT DOCUMENTS

| | | | |
|---|---|---|---|
| 4,283,124 | 8/1981 | Motsumura | 351/206 |
| 4,400,144 | 2/1990 | Kobayashi | 351/206 |
| 4,673,264 | 6/1987 | Takahashi | 351/206 |
| 4,743,107 | 5/1980 | Aizu et al. | 351/206 |
| 4,813,778 | 3/1980 | Madate et al. | 351/208 |

Primary Examiner—William E. Kamm
Assistant Examiner—Scott R. Akers
Attorney, Agent, or Firm—Bruce L. Adams; Van C. Wilks

[57] ABSTRACT

A fundus examining device is provided in which laser light from a laser light source is deflected for scanning in two dimensions over an eye fundus of an eye being examined and light reflected from the eye fundus is photoelectrically detected with a photodetector to obtain fundus information. The fundus examining device includes an optical system for observing an anterior portion of the eye which is illuminated by illuminating light to determine how the pupil of the eye is dilated. To this end, an objective mirror is provided which reflects light of the wavelength of the laser beam but is transparent to the illuminating light. The objective mirror reflects the deflected laser beam to illuminate the fundus of the eye, while guiding light from the illuminated anterior portion of the eye to the observing optical system.

5 Claims, 2 Drawing Sheets

FUNDUS EXAMINATION DEVICE

BACKGROUND OF THE INVENTION

1. Field of the Invention

This invention relates to a fundus examination device, and particularly to an improvement of an electronic ophthalmoscope which uses laser light as its light source, in which the laser beam is deflected for scanning in two dimensions to illuminate the fundus of the eye being examined, and light reflected from the eye fundus is photoelectrically detected and processed to obtain fundus information.

2. Description of the Prior Art

Conventionally, examination of the fundus of the eye is widely carried out by either the method of the physician directly examining the fundus of the patient's eye using a device called a funduscope or the method of photography using a special camera called a fundus camera. Furthermore, with advances in electronic technology in recent years, the photographic film of a conventional fundus camera is giving way to methods using a camera tube or other photoelectric transducer to directly obtain fundus information as an electrical signal, which may be then processed, stored or displayed on a TV monitor.

Against this background, the first laser-scanning electronic ophthalmoscope was developed in the United States (see U.S. Pat. No. 4,213,678 and Applied Optics, Vol. 19 (1980), p. 2,991) and had many benefits, attracting much attention.

Namely, a laser is used as a light source of a previously studied cathode-ray-tube flying-spot scanning fundus imaging device. Furthermore, light is permitted to go through only a small region in the center of the pupil, and light reflected from the eye fundus is obtained from a wide region around the pupil, photoelectrically converted and amplified to give low-illuminance yet high signal-to-noise ratio images of the eye fundus which can be projected onto TV monitors in real time. Moreover, the amount of fluorescent dye which must be intravenously injected during fluorescent fundus imaging may be greatly reduced. In addition, by modulating the incident scanning light, retinal function may be examined while observing images of the eye fundus, thus serving as a so-called fundus perimeter or fundus analyzer. Furthermore, that invention provides the potential of obtaining a superior diagnostic device from the standpoint of making the striking depth of field with the laser beam, eliminating corneal reflections due to polarization, employing its monochromaticity and providing expansion into therapeutic machines (coagulators).

This new type of ophthalmoscope has since been subject to many further experiments and improvements by research groups around the world. Among them, the present inventors have invented, developed and applied for a patent on an extremely innovative stereoscopic shape-measuring device based on a completely new principle which allows three-dimensional measurement of an eye fundus in vivo (see Japanese Patent Application Public Disclosure No. 1(1989)-113605, corresponding to U.S. Pat. No. 4,900,144). That invention employs a means of detecting displacement of the position of the focus of light reflected from the subject and a signal processing means which eliminates the effects of the optical reflection characteristics of the subject, thereby extracting three-dimensional stereoscopic information from the subject. The invention enables an extremely short measurement and processing time, high accuracy and reproducibility of measurement, and moreover, information regarding the normal two-dimensional reflection characteristics can be obtained at the same time as the three-dimensional information. Thus the invention provides superior technology for stereoscopic shape measurement of the in-vivo eye fundus in general and measurement of the optic disk for early diagnosis of glaucoma in particular.

However, when applying this stereoscopic shape-measuring device to an actual in-vivo eye fundus, as is apparent from considering the principle of measurement, the accuracy of measurement is degraded if the state of dilation of the pupil is poor. Namely, in the device disclosed in Japanese Patent Application Public Disclosure No. 1(1989)-113605), changes in the contour of the fundus subject to examination are detected as changes in the flux of light passing through detection slits, but if the state of dilation of the pupil is poor, then the changes in light flux are reduced. Therefore, determination of whether the three-dimensional shape data obtained with this device is valid or not necessitates a judgmental check of the state of dilation of the pupil. However, the device disclosed in Japanese Patent Application Public Disclosure No. 1(1989)-113605) does not provide a function for measuring the diameter of the pupil in the anterior portion of the eye, so the examiner must check the state of dilation of the patient's pupil either visually or using a separate method or device.

In addition, while unrelated to three-dimensional measurement, in normal two-dimensional fundus imaging methods typically using laser scanning, it is possible to display an image of the fundus on a monitor screen in real time using low-intensity illumination which causes little discomfort to the patient. However, when imaging the fundus using visible, short-wavelength laser light in particular, after positioning the device with respect to the eyeball as in conventional non-pupil-dilating fundus cameras, the eye is flash-illuminated with laser light for only the time required for one frame or several frames at a time to record an image of the fundus in memory. This imaging method has been found to be effective from the standpoint of reducing discomfort in the patient. In this case, if the positioning of the device to the eyeball is insufficient, flare due to light reflected from the anterior portion of the eye will impinge on the image of the fundus and result in a loss of picture quality. Although the process of observing the anterior portion of the eye is important for positioning the device to the eyeball, conventional laser-scanning fundus examination devices are not provided with functions for observing the anterior portion of the eye, making the adjustment of the device position with respect to the eyeball difficult.

Naturally, techniques for observing the anterior portion of the eye are employed in the traditional non-pupil-dilating fundus cameras of the past, namely by redirecting the light path somewhere in the midst of the camera's optical system or by inserting an auxiliary lens into the optical system and thereby observing the anterior portion of the eye. Naturally, these sorts of techniques can also be employed in the laser-scanning type of fundus imaging system. However, these traditional techniques involve the bother of mechanically redirecting the light path or inserting and removing lenses and moreover the fundus and the anterior portion of the eye cannot be observed at the same time, so they are not necessarily the ideal solution.

SUMMARY OF THE INVENTION

Principle objects of this invention are to solve the aforementioned problems by providing a new laser-scanning fundus examination device which simplifies the positioning of the optical system of the device in relation to the eyeball of the eye being examined when imaging an eye fundus using flash illumination, and is provided with a function for examining the anterior portion of the eye together with a function for imaging the fundus so that the state of dilation of the pupil can be reliably examined to check the validity of data during three-dimensional measurements.

According to the invention, a fundus examining device is provided in which laser light from a laser light source is deflected for scanning in two dimensions over an eye fundus of an eye being examined, and light reflected from the eye fundus is photoelectrically detected with a photodetector to obtain fundus information. The fundus examining device comprises a laser light source for producing a laser beam; means for deflecting the laser beam to scan across the eye fundus; an illumination light source for producing illuminating light which illuminates an anterior portion of the eye being examined; an optical system for observing the illuminated anterior portion of the eye being examined; and an optical element which reflects light of the wavelength of the laser beam but is transparent to the illuminating light; wherein the optical element reflects the deflected laser beam to illuminate the fundus of the eye being examined, while guiding light from the illuminated anterior portion of the eye to the observing optical system.

The fundus examining device further comprises a laser light source for producing a laser beam; means for deflecting the laser beam to scan across the eye fundus; a first optical system for illuminating the fundus of the eye being examined with the laser beam which is deflected by the deflecting means; means for detecting displacement of the position of the focus of light reflected from the eye fundus to derive therefrom eye fundus shape-related information in the direction of the optic axis which is perpendicular to the scanning direction of the deflecting means; signal processing means for removing the effects of the optical reflection characteristics of the fundus from the output signal of the detecting means; an illumination light source for producing illuminating light having a wavelength different than the wavelength of the laser beam to illuminate an anterior portion of the eye being examined; and a second optical system for observing the illuminated anterior portion of the eye being examined.

Furthermore, the fundus examining device comprises a laser light source for producing a laser beam; means for deflecting the laser beam to scan across the eye fundus; an objective mirror which reflects the laser beam deflected by the deflecting means but is transparent to light of a wavelength different than the wavelength of the laser beam; means for detecting displacement of the position of the focus of light reflected from the eye fundus to derive therefrom eye fundus shape-related information in the direction of the optic axis which is perpendicular to the scanning direction of the deflecting means; signal processing means for removing the effects of the optical reflection characteristics of the fundus from the output signal of the detecting means; an illumination light source for producing illuminating light having a wavelength different than the wavelength of the laser beam to illuminate an anterior portion of the eye being examined; and an optical system for observing the illuminated anterior portion of the eye being examined; wherein light from the illuminated anterior portion of the eye being examined is guided to the observing optical system via the objective mirror.

With the above structure, the optical element which reflects light of the wavelength of the laser beam but is transparent to the illuminating light is provided, and this optical element comprises an objective mirror in one preferred embodiment of the invention. An image of the fundus is obtained from the laser light reflected from this objective mirror, while the light which passes through the objective mirror is used to obtain an image of the anterior portion of the eye, so the bothersome manipulation of the optical system required by traditional non-pupil-dilating fundus cameras of the past is eliminated and the anterior portion of the eye being examined can be continuously observed. Therefore, positioning of the optical system of the device in relation to the eyeball of the eye being examined is simplified when imaging a fundus using flash illumination, and the state of dilation of the pupil can be reliably examined during three-dimensional measurement of the fundus.

Furthermore, by using an objective mirror when observing the fundus, the problem of surface reflections which appear when using an objective lens is eliminated. In addition, since an image of the anterior portion of the eye is always visible, the device may be employed as an electronic pupillometer. For these and other reasons, the present invention may be embodied as an extremely practical laser-scanning fundus examination device.

BRIEF DESCRIPTION OF THE DRAWINGS

The objects and features of the present invention will become more apparent from the accompanying drawings and the following detailed description of the invention.

DETAILED DESCRIPTION OF THE PREFERRED EMBODIMENTS

Figure 1:
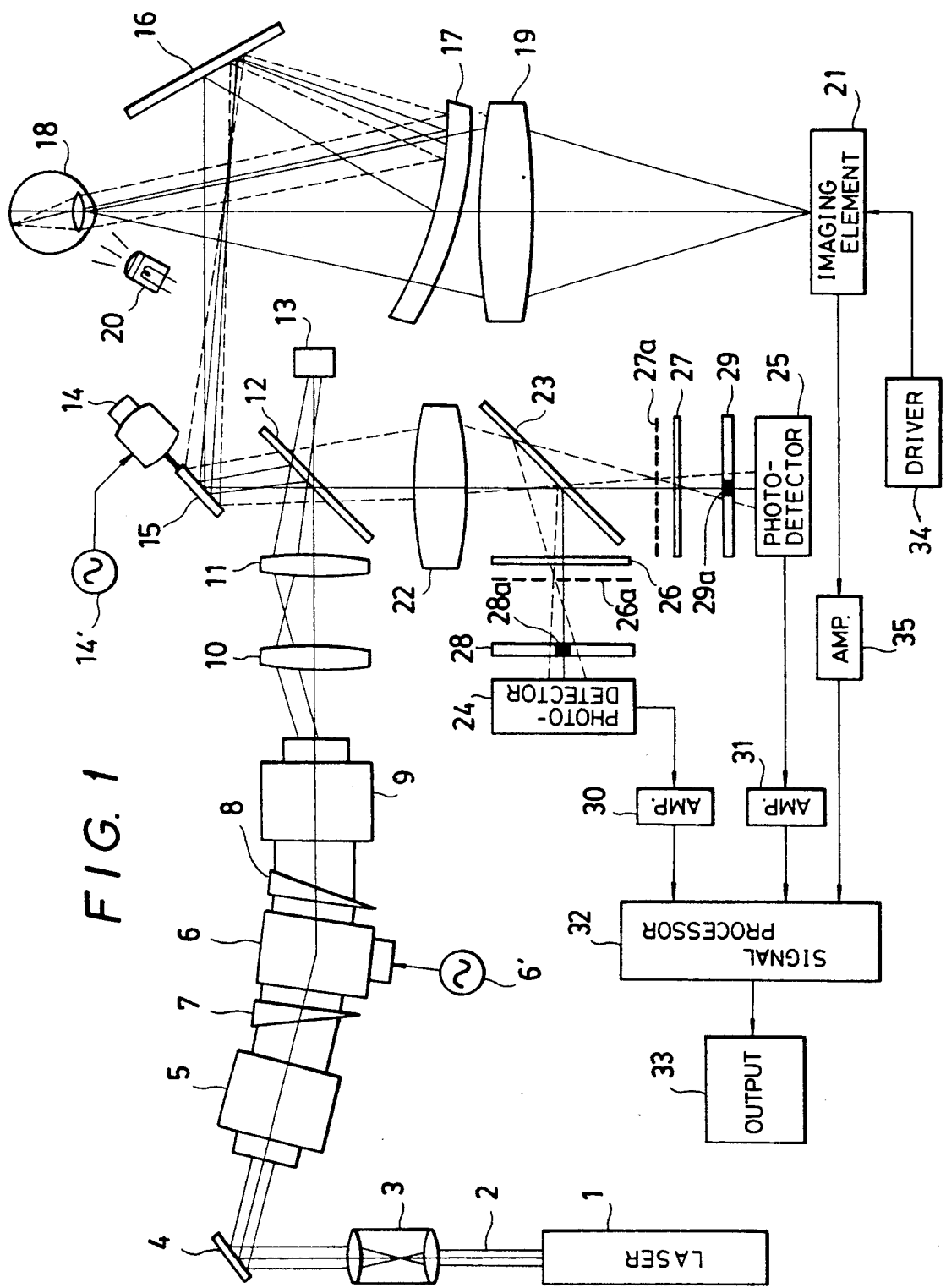
FIG. 1 is a structural diagram showing the overall structure of the optical system of a fundus examination device according to the present invention.
Figure 2:
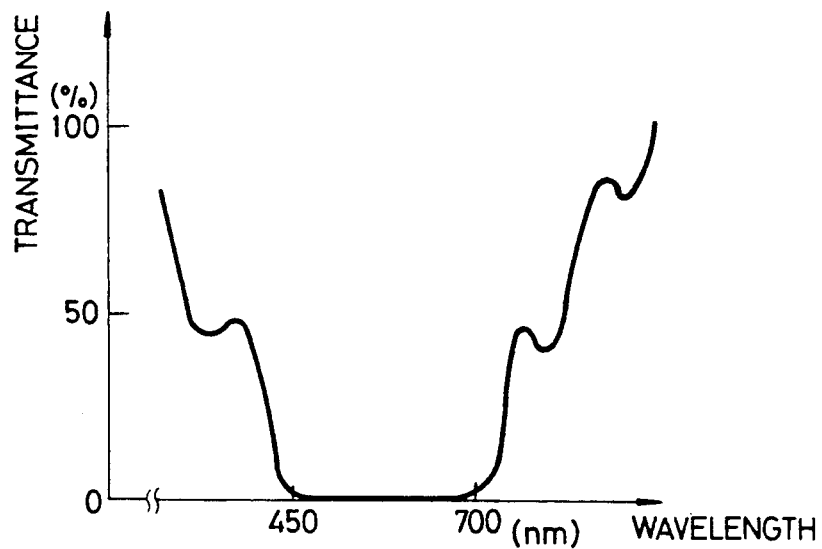
FIG. 2 is a graph of the spectral response of the optical element.
Figure 3:
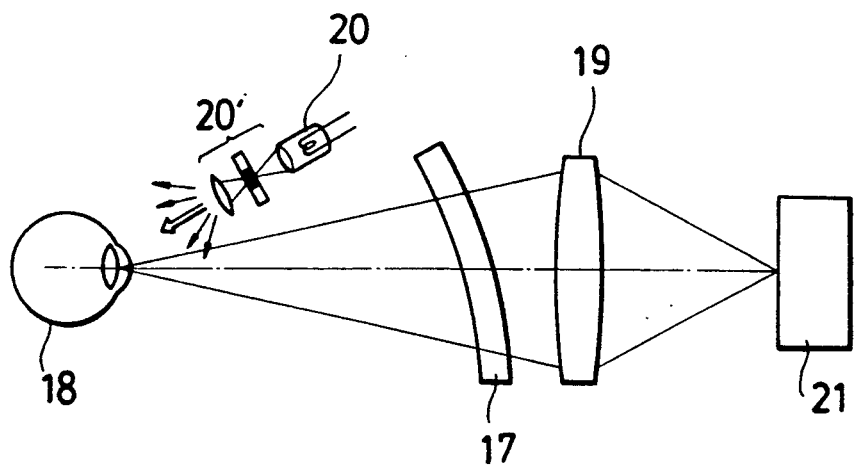
FIG. 3 is a structural diagram of the optical system which illuminates the anterior portion of the eye being examined.

The above and other features of the present invention will become apparent from the following description made with reference to FIGS. 1 through 3.

FIG. 1 illustrates the overall structure of the optical system and electrical system of a fundus examination device according to the invention. In FIG. 1, 1 is an argon (Ar+), helium-neon (He-Ne) or other laser which acts as a source of visible laser light. The laser beam 2 from the laser light source is expanded to a certain size with a beam expander 3 and reflected by a mirror 4 into a lens 5. The lens 5 is a combination of a plurality of cylindrical lenses used to shape the laser beam and direct it into a rectangular aperture in an acoustooptic deflector (hereinafter AOD) 6.

In order to correct the wavelength dependence of the angles for the laser beam incidence and emergence with respect to the AOD, prisms 7 and 8 are disposed at the front and rear of the AOD 6. Note that these prisms are not necessarily required if a monochromatic laser beam is used. The AOD 6 is actuated by a signal source 6', whereby the laser beam is deflected to scan at a frequency of 15.75 kHz, for example, corresponding to the horizontal scanning of a normal television system. The laser light deflected by the AOD 6 in one direction (the horizontal direction) is then passes through a lens 9 of a construction similar to that of lens 5 and reshaped into its original round beam from the rectangular beam matching the aperture of the AOD 6.

The scanning light exiting from the lens 9 passes through lenses 10 and 11 and reaches a beam splitter 12 which reflects part of the light and allows the remainder to pass through. The beam splitter 12 may be, for example, a polarizing beam splitter or a non-polarizing beam splitter of roughly 25% reflectance and 75% transmittance. The laser light which passes through the beam splitter 12 enters a photodetector 13 comprising a photodiode or the like, the output signal of which is used to monitor the power of the laser light.

On the other hand, the laser light reflected by the beam splitter 12 is guided to a mirror 15 mounted on a galvanometer 14. The galvanometer-mirror 15 is actuated by a signal source 14', whereby the laser beam is deflected to scan at a frequency of 60 Hz, for example, corresponding to the vertical scanning of a television system, and its scanning direction is perpendicular to the direction of scanning controlled by the AOD 6. The thus-formed two-dimensional laser rasters corresponding to television scanning lines is then reflected by a mirror 16 and an objective mirror 17 and projected through the center of the pupil of the eye 18 being examined.

As is evident in the spectral response of the objective mirror 17 used here, illustrated in FIG. 2, the objective mirror 17 reflects 99% of the incident light at visible wavelengths, but is almost transparent to infrared light, reflecting almost no infrared component. Such an optical characteristic may be obtained by means of vacuum-deposition technology used to create coatings of dielectric multilayers. The eye 18 being examined is illuminated by an infrared illumination light source 20 comprising an infrared lamp, lenses, filters and the like. Behind the objective mirror 17 is disposed a lens 19. This lens 19 is used to monitor the anterior portion of the eyeball by forming an image of the anterior portion of the eye 18 being examined on an imaging plane of CCD or other infrared imaging elements 21.

At this time, as shown in FIG. 3, if an additional optical system 20' comprising, for example, a lens, ND filter and the like is used to illuminate the eye 18 being examined with the purpose of projecting an index image, the distance between the eyeball of the eye being examined and the device (the working distance) may be determined from the image output from the infrared imaging elements 21. Namely, the principle of triangulation can be used to check the working distance by seeing, for example, if a dark portion due to the additional optical system 20' appears on the center of the cornea in the image of the anterior portion of the eye.

On the other hand, the light reflected from the fundus illuminated by the visible laser scanning light (shown by dotted lines in FIG. 1) is reflected and guided back by the objective mirror 17, mirror 16, and galvanometer-mirror 15 to pass through the beam splitter 12 and a lens 22, after which it is divided in half by a half mirror 23, each half being detected by one of photodetectors 24 or 25.

Detection slits 26 and 27 are disposed near focusing planes (conjugate planes of the fundus of the eye being examined) 26a and 27a between the half mirror 23 and photodetectors 24 and 25. Disposed on the front surfaces of photodetectors 24 and 25 are filters 28 and 29 which are transparent to only light of the same wavelength as the laser light being used. Note that in order to prevent photodetectors 24 and 25 from detecting light reflected directly from the anterior portion of the eye 18 being examined, the center portions 28a and 29a of filters 28 and 29 are marked. Furthermore, in this sort of optical system using an objective mirror 17, there is no need for the black spots (light stops) used to eliminate reflections from the surface of the objective lens, as was required in the optical system the present inventor had disclosed in the Patent Application Public Disclosure as earlier described, so the loss of light flux and problems with positioning of the black spots in the optical system are completely eliminated.

Detection slits 26 and 27 are used for making three-dimensional measurements of the fundus based on the principles described in the above-mentioned Patent Application Public Disclosure, and U.S. Pat. No. 4,900,144 and these two are disposed near but slightly in front and behind their respective positions 26a and 27a conjugate to the fundus. Namely, when contours in the fundus cause the fundus-conjugate position near the slit to vary slightly, the focal point of light reflected from the fondus will vary and a change will appear in the output signal from the photodetectors which detect light from the fundus after passing through the slit. For example, if there is a depression on the fundus, a difference in intensity of the output signals from the two photodetectors will appear, so the depth of the depression in the fundus can be determined by eliminating information on the reflectance of the fundus from the output signals of the two. Now, assuming that the output signal intensity of the two photodetectors are $I_1$ and $I_2$ and $I_0(x,y)$ is the reflection light intensity at location x,y on the fundus, then these variables related to the reflectance of the fundus can be expressed mathematically as $$I_1 = f_1(z) \times I_0(x,y)$$

$$I_2 = f_2(z) \times I_0(x,y)$$

where $f_1(z)$ and $f_2(z)$ are functions of the distance z in the direction of the optic axis of the optical system, appearing due to the presence of the slits. Therefore, since $I_1/I_2 = f_1(z)/f_2(z)$, if a division operation is performed on the output signals from the two photodetectors, information related to the distance z in the direction of the optic axis, namely the degree of changes in the contour of the fundus can be extracted and determined regardless of the intensity of reflection from the fundus.

Or since $$(I_1 - I_2)/(I_1 + I_2) = (f_1(z) - f_2(z))/(f_1(z) + f_2(z))$$

information related to z can be detected by a combination of the arithmetic operations of addition, subtraction and division.

The output signals from photodetectors 24 and 25, after being amplified to a specified level by amplifiers 30 and 31, are provided as inputs to a signal processing device 32 which carries out the aforementioned division operation and other arithmetic operations to extract information on the contour of the fundus (stereoscopic shape data). The signal processing device 32 employs a built-in microprocessor and software processing to generate three-dimensional graphic patterns or the like from the stereoscopic shape data thus obtained, and the final results are displayed on a TV monitor or other output device 33.

On the other hand, the infrared imaging elements 21 onto which an image of the anterior portion of the eye being examined is formed are controlled by a dedicated driving circuit 34 for the CCDs or the like. Its output signal, after being amplified to a specified level by amplifier 35, is displayed through the signal processing device 32 on the output device 33 as an image of the anterior portion of the eye being examined. For example, if two TV monitors are used as the output device 33, both an image of the anterior portion of the eye being examined and an image of the fundus can be displayed and observed simultaneously, or if a function for creating multiple windows is added to the signal processing device 32, the same effect can be attained using one TV monitor.

Since an image of the anterior portion of the eye being examined can always be obtained from the output signal from the imaging elements 21, the state of dilation of the pupil can be conveniently checked, and when carrying out three-dimensional measurements of the fundus, the validity of the measurements can be reliably checked while observing the data. In addition, positioning the device to the eyeball together with adjustment of the optic axis and the working distance can be carried out conveniently using the image of the anterior portion of the eye, so a device having such an optical system can be also employed as an electronic pupillometer to measure pupillary reflex and the like.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A fundus examining device for examining an eye fundus of an eye, comprising:
    a laser light source for producing a laser beam;
    means for deflecting the laser beam to scan across an eye fundus of an eye being examined;
    an illumination light source for producing illuminating light which illuminates an anterior portion of the eye being examined;
    an optical system for observing the illuminated anterior portion of the eye being examined; and
    an optical element which reflects light of the wavelength of the laser beam, but is transparent to the illuminating light, the optical element being positioned to reflect the deflected laser beam to illuminate the fundus of the eye being examined and to guide the illuminating light from the illuminated anterior portion of the eye to the observing optical system.

2. The fundus examining device according to claim 1, in which the optical element comprises an objective mirror.

3. A fundus examining device for examining an eye fundus of an eye, comprising:
    a laser light source for producing a laser beam;
    means for deflecting the laser beam to scan across an eye fundus of an eye being examined;
    a first optical system for illuminating the fundus of the eye being examined with the laser beam which is deflected by the deflecting means;
    means for detecting displacement of the position of the focus of light reflected from the eye fundus to derive therefrom eye fundus shape-related information in the direction of the optic axis which is perpendicular to the scanning direction of the defecting means and producing a corresponding output signal;
    signal processing means for removing the effects of the optical reflection characteristics of the fundus from the output signal of the detecting means;
    an illumination light source for producing illuminating light having a wavelength different than the wavelength of the laser beam to illuminate an anterior portion of the eye being examined;
    a second optical system for observing the illuminated anterior portion of the eye being examined; and
    an optical element which reflects light of the wavelength of the laser beam but is transparent to the illuminating light, the optical element being positioned to reflect the deflected laser beam to illuminate the fundus of the eye and direct light reflected from the eye fundus to the detecting means and to guide the illuminating light from the illuminated anterior portion of the eye to the second optical system.

4. The fundus examining device according to claim 2, in which the optical element comprises an objective mirror.

5. A fundus examining device for examining an eye fundus of an eye, comprising:
    a laser light source for producing a laser beam;
    means for deflecting the laser beam to scan across an eye fundus of an eye being examined;
    an objective mirror which reflects light of the wavelength of the laser beam but is transparent to light to a wavelength different than the wavelength of the laser beam, the objective mirror being positioned to reflect the deflected laser beam to illuminate the fundus of the eye being examined;
    means for detecting displacement of the position of the focus of light reflected from the eye fundus to derive therefrom eye fundus shape-related information in the direction of the optical axis which is perpendicular to the scanning direction of the deflecting means and producing a corresponding output signal;
    signal processing means for removing the effects of the optical reflection characteristics of the fundus from the output signal of the detecting means;
    an illumination light source for producing illuminating light having a wavelength different than the wavelength of the laser beam to illuminate an anterior portion of the eye being examined; and
    an optical system for observing the illuminated anterior portion of the eye being examined;
    wherein the objective mirror is positioned to guide the illuminating light from the illuminated anterior portion of the eye to the observing optical system.

* * * * *